US006605292B1

(12) United States Patent
Ueda et al.

(10) Patent No.: US 6,605,292 B1
(45) Date of Patent: *Aug. 12, 2003

(54) SHEETS WITH A VOLATILE COMPOUND

(75) Inventors: Minoru Ueda, Toyonaka (JP); Yoko Saito, Osaka (JP)

(73) Assignee: Sumitomo Chemical Company, Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/186,642

(22) Filed: Nov. 6, 1998

(30) Foreign Application Priority Data

Nov. 11, 1997 (JP) ............................... 9-308790

(51) Int. Cl.⁷ ............................... A01N 25/34
(52) U.S. Cl. .................. 424/416; 424/DIG. 8
(58) Field of Search ................ 424/405, 416, 424/411, DIG. 8

(56) References Cited

U.S. PATENT DOCUMENTS

| 131,242 | A | * | 9/1872 | Baquol ........................ 424/416 |
| 3,785,561 | A | | 1/1974 | Confino et al. ............... 239/60 |
| 4,661,388 | A | * | 4/1987 | Charbonneau |
| 4,678,206 | A | * | 7/1987 | Leahan |
| 4,751,934 | A | * | 6/1988 | Moir et al. |
| 4,985,457 | A | | 1/1991 | Kishino et al. |
| 6,185,862 | B1 | * | 2/2001 | Nelson |

FOREIGN PATENT DOCUMENTS

| EP | 0576270 | B1 | 12/1993 |
| EP | 0792581 | A1 | 9/1997 |
| JP | 57131550 | * | 8/1982 |

OTHER PUBLICATIONS

Database WPI Derwent Publications Ltd., London, GB; AN 94–290503 XP002094067.

* cited by examiner

*Primary Examiner*—Edward J. Webman
(74) *Attorney, Agent, or Firm*—Birch, Stewart, Kolasch & Birch, LLP

(57) ABSTRACT

The present invention provides the sheets preserving a compound being volatile at room temperature, wherein plural sheets comprising of the compound being volatile at room temperature are constructed as layers. The volatile compound may be selected from the group consisting of N,N-diethyl-m-toluamide, carane-3,4-diol, and pyrethroid compounds such as 1-ethynyl-2-methyl-2-pentenyl (1R)-3-(2-methyl-1-propenyl)-2,2-dimethylcyclopropanecarboxylate; 2,3,5,6-tetrafluorobenzyl (1R)-trans-3-(2,2-dichlorovinyl)-2,2-dimethylcyclopropanecarboxylate; 1-ethynyl-2-methyl-2-pentenyl 3-(2-chloro-2-fluorovinyl)-2,2-dimethylcyclopropanecarboxylate; 2,3,5,6-tetrafluoro-4-methylbenzyl 3-(2-methyl-1-propenyl)-2,2-dimethylcyclopropanecarboxylate; 2,3,5,6-tetrafluoro-4-methylbenzyl 3-(2-chloro-2-fluorovinyl)-2,2-dimethylcyclopropanecarboxylate; and 2,3,5,6-tetrafluoro-4-methylbenzyl 3-(1-propenyl)-2,2-dimethylcyclopropanecarboxylate.

The sheets can continue to volatize an ingredient (a pest-controlling agent, perfume, insecticidal compound, etc. which are volatile at room temperature) after a long period of time passes.

12 Claims, No Drawings

SHEETS WITH A VOLATILE COMPOUND

FIELD OF THE INVENTION

The present invention relates to a stack of sheets preserving a compound or compounds being volatile at room temperature (hereinafter referred to as volatile compound) and particularly when the volatile compound is an insecticidal or aroma chemical compound.

BACKGROUND OF THE INVENTION

The art in which a sheet preserves a volatile compound is well known. Such a sheet usually is placed where the surrounding environment fit the purpose of the preserved compound and is set to vaporize the preserved compound(s). However, the employment of a single sheet has limits and may be considered unsatisfactory. A large part of the preserved compound vaporizes after a relatively short period of time and cannot be efficient to vaporize the same compound for a relatively long period of time. Therefore, it would be a distinct advantage if a sheet model can vaporize the preserved compound for a long period of time. The longer vaporization period will allow the sheet model to extend its uses as an air refresher, insecticide and/or pest repellent.

The goal of the present invention is to have a stack of sheets preserving a volatile compound, to which comprise the ability to vaporize the preserved volatile compound after a relatively long period of time.

DETAILED DESCRIPTION OF INVENTION

The sheets of the present invention are employed as a stack of sheets. By stacking plural sheets that preserve the volatile compound, vaporization continues after a long period of time. As the number of sheets increase, the vaporization within the sheets that preserve the volatile compound is suppressed, favorably causing the compound to continually vaporize after a long period of time. The number of sheets in the present invention is generally at least 10 sheets, for example 10 to 1000 sheets, preferably having at least 20 sheets, for example 20 to 500 sheets.

The size of the sheet preserving the volatile compound is not especially limited but the object of use, variation of sheet material, variation of the compound, and a consideration for the surrounding environment in setting may be factors influencing the size of the sheet. To generally fulfill these factors, a sheet of 20 to 1000 $cm^2$ usually is employed. The thickness of the said sheet is also not limited, but a thickness of 20 to 200 $\mu$m may be preferable.

Materials to fabricate the sheet employed in the present invention are also not especially limited, and for example, papers; synthetic resins such as polyesters and polyamides; aluminum; and so on may be employed. Furthermore, employing sheets wherein synthetic resin(s) cover(s) the surface of paper or aluminum is possible.

The compound in the present invention may be any volatile compound that has the ability to readily vaporize at room temperature or more particularly, when the vapor pressure is at least $1\times10^{-4}$ mmHg at 20° C. Such volatile compounds may be the active ingredient found in insecticides, acaricides, noxious pest repellents that are pest controlling compounds or the active ingredient found in perfumes that are aroma chemicals.

Specific examples for insecticidal compounds recited above are N,N-diethyl-m-toluamide, carane-3,4-diol, and pyrethroid compounds such as 1-ethynyl-2-methyl-2-pentenyl (1R)-3-(2-methyl-1-propenyl)-2,2-dimethylcyclopropanecarboxylate (common name: empenthrin); 2,3,5,6-tetrafluorobenzyl (1R)-trans-3-(2,2-dichlorovinyl)-2,2-dimethylcyclopropanecarboxylate (common name: transfluthrin); 1-ethynyl-2-methyl-2-pentenyl 3-(2-chloro-2-fluorovinyl)-2,2-dimethylcyclopropanecarboxylate; 2,3,5,6-tetrafluoro-4-methylbenzyl 3-(2-methyl-1-propenyl)-2,2-dimethylcyclopropanecarboxylate; 2,3,5,6-tetrafluoro-4-methylbenzyl 3-(2-chloro-2-fluorovinyl)-2,2-dimethylcyclopropanecarboxylate; and 2,3,5,6-tetrafluoro-4-methylbenzyl 3-(1-propenyl)-2,2-dimethylcyclopropanecarboxylate.

To preserve the volatile compound in the employed sheet, the compound itself or a solution comprising the compound is impregnated or soaked onto the sheet. The said solution may be any solution wherein the compound is dissolved in any solvent such as acetones and/or alcohols (for example, methanol, ethanol, isopropyl alcohol) and so on. An unlimited amount of the volatile compound may be preserved in the sheet but the object of use, variation of sheet material, variation of compound, and a consideration for the surrounding environment are factors that may influence the amount of preservation. In the situation of utilizing the insecticidal compound of empenthrin, 0.5 to 20 grams of the said insecticidal compound per 1 $m^2$ of sheet surface area (0.5 to 20 $g/m^2$) may be utilized.

The method to incorporate the compound is not limited. The volatile compound may be impregnated or soaked to the sheet(s) before or after the sheets are stacked together.

To produce high results with the present invention, the most outer layering sheet may be separated from the stack, so the inner sheet is left to be exposed to the surrounding environment. The most outer layering sheet tends to loose the ability to vaporize first, and should be separated when vaporization no longer continues in the most outer sheet. Once the outer sheet is separated, the inner sheet wherein a copious amount of the compound still exists, may be exposed to the environment.

The present invention also takes various forms of construction. In the event of constructing the sheets to be a bound stack, an adhesive agent may be disposed on one side of each sheet and a releasing agent may be disposed on the other side. The side wherein the adhesive agent has been disposed may then unite to a side from another sheet in which the releasing agent has been disposed. Free sheets may then be united with the plurality of sheets which have already been united. Accordingly, the most outer layer is made to be easily detachable. A "memo pad-like calendar" which is a construction wherein the sheets are categorized by a day or days and are torn away from the calendar after the day or days pass, is produced in similar fashion.

EXAMPLES

Hereinafter, the present invention will be explained in detail with the examples.

Example 1

By impregnating a: 30 cm×20 cm "memo pad-like calendar" (365 sheets of paper) with 1 g of empenthrin (a pyrethroid compound), the sheets with a volatile compound for the present invention are obtained. The obtained sheets with a volatile compound may be utilized by locating on pillars and/or walls indoors, to control flies and mosquitoes indoors.

Example 2

Fifty grams of 1-ethynyl-2-methyl-2-pentenyl (1R)trans-3-(2-chloro-2-fluorovinyl)-2,2- dimethylcyclopropanecarboxylate, was impregnated onto a 30 cm×20 cm "memo pad-like calendar" (365 sheets of paper) in order to obtain the sheets with a volatile compound for the present invention. The obtained sheets with a volatile compound may be utilized by locating on pillars and/or walls indoors, to control flies and mosquitoes indoors.

Example 3

Twenty grams of 2,3,5,6-tetrafluoro-4-methylbenzyl (1R)-trans-3-(2-methyl-1-propenyl)-2,2-dimethylcyclopropanecarboxylate was impregnated onto a 30 cm×20 cm "memo pad-like calendar" (365 sheets of paper) in order to obtain the sheets with a volatile compound for the present invention. The obtained sheets with a volatile compound may be utilized by locating on pillars and/or walls indoors, to control flies and mosquitoes indoors.

Example 4

Ten grams of 2,3,5,6-tetrafluoro-4-methylbenzyl 3(2-chloro-2-fluorovinyl)-2,2-dimethylcyclopropanecarboxylate was impregnated onto a 30 cm×20 cm "memo pad-like calendar" (365 sheets of paper) in order to obtain the sheets with a volatile compound for the present invention. The obtained sheets with a volatile compound may be utilized by locating on pillars and/or walls indoors, to control flies and mosquitoes indoors.

Example 5

Five grams of 2,3,5,6-tetrafluoro-4-methylbenzyl (1R)-trans-3-((Z)-1-propenyl)-2,2-dimethylcyclopropanecarboxylate was impregnated onto a 30 cm×20 cm "memo pad-like calendar" (365 sheets of paper) in order to obtain the sheets with a volatile compound for the present invention. The obtained sheets with a volatile compound may be utilized by locating on pillars and/or walls indoors, to control flies and mosquitoes indoors.

Example 6

With thirty 10 cm×10 cm sheets, 200 mg of a rose perfume was applied to the side wherein the releasing agent is disposed. After pasting an adhesive agent to the backside of the side wherein the releasing agent has been disposed, the side wherein the releasing agent has been disposed and a side from another sheet wherein the adhesive agent has been pasted were layered to unite. Accordingly, the sheets with a volatile compound for the present invention is obtained. The obtained sheets with a volatile compound may be utilized by locating in bathrooms, men's and ladies' rooms as an aromatic sample.

What is claimed is:

1. An assembly of sheets wherein each sheet contains an insecticidal compound which is volatile at room temperature, wherein said assembly of sheets is comprised of a plurality of said sheets which are impregnated or soaked with said compound assembled as detachable layers and each said sheet having an adhesive disposed on one side thereof, whereby said sheets are caused to be adhered together to form said assembly of sheets.

2. The assembly according to claim 1, wherein said compound is selected from the group consisting of N,N-diethyl-m-toluamide; carane-3,4-diol; 1-ethynyl-2-methyl-2-pentenyl (1R)-3-(2-methyl-1-propenyl)-2,2-dimethylcyclopropanecarboxylate; 2,3,5,6-tetrafluorobenzyl (1R)-trans-3-(2,2-dichlorovinyl)-2,2-dimethylcyclopropanecarboxylate; 1-ethynyl-2-methyl-2-pentenyl 3-(2-chloro-2-fluorovinyl)-2,2-dimethylcyclopropanecarboxylate; 2,3,5,6-tetrafluoro-4-methylbenzyl 3-(2-methyl-1-propenyl)-2,2-dimethylcyclopropanecarboxylate; 2,3,5,6-tetrafluoro-4-methylbenzyl 3-(2-chloro-2-fluorovinyl)-2,2-dimethylcyclopropane-carboxylate; and 2,3,5,6-tetrafluoro-4-methylbenzyl 3-(1-propenyl)-2,2-dimethylcyclopropanecarboxylate.

3. The assembly according to claim 1, wherein the number of sheets in said assembly is 10 or more.

4. The assembly according to claim 1, wherein each said sheet has a releasing agent disposed on a side opposite the side on which said adhesive is located, whereby the side with the adhesive and a side of an adjacent sheet having said releasing agent are positioned together to unite said sheets together.

5. The assembly according to claim 1 having a layered construction as a memo pad-like calendar.

6. The assembly according to claim 4, wherein the number of sheets in said assembly is 10 or more.

7. A method of vaporizing a controlled amount of a volatile insecticidal compound, which comprises allowing said volatile insecticidal compound to vaporize from an outermost sheet in said assembly defined by claim 1, and thereafter removing said outer sheet thereby exposing an inner sheet to the surrounding environment.

8. The method according to claim 7, wherein said compound is selected from the group consisting of N,N-diethyl-m-toluamide; carane-3,4-diol; 1-ethynyl-2-methyl-2-pentenyl (1R)-3-(2-methyl-1-propenyl)-2,2-dimethylcyclopropanecarboxylate; 2,3,5,6-tetrafluorobenzyl (1R)-trans-3-(2,2-dichlorovinyl)-2,2-dimethylcyclopropanecarboxylate; 1-ethynyl-2-methyl-2-pentenyl 3-(2-chloro-2-fluorovinyl)-2,2-dimethylcyclopropanecarboxylate; 2,3,5,6-tetrafluoro-4-methylbenzyl 3-(2-methyl-1-propenyl)-2,2-dimethylcyclopropanecarboxylate; 2,3,5,6-tetrafluoro-4-methylbenzyl 3-(2-chloro-2-fluorovinyl)-2,2-dimethylcyclopropanecarboxylate; and 2,3,5,6-tetrafluoro-4-methylbenzyl 3-(1-propenyl)-2,2-dimethylcyclopropanecarboxylate.

9. The method according to claim 7, wherein said sheets are present in said assembly in a stack of 10 or more layered sheets comprising an adhesive on one side of said sheets and a releasing agent on the other side of said sheets, and wherein the adhesive on the side of at least one of said sheets is positioned together with the releasing agent on the side of another of said sheets.

10. The method according to claim 7, wherein said sheets ion said assembly are present in a stack of 10 or more sheets, and wherein each sheet in said stack contains said volatile compound.

11. The assembly according to claim 3, wherein the number of sheets in said assembly is 10 to 1000.

12. The assembly according to claim 3, wherein the number of sheets in said assembly is 20 to 500.

* * * * *